US011344221B2

(12) United States Patent
Gliner et al.

(10) Patent No.: US 11,344,221 B2
(45) Date of Patent: May 31, 2022

(54) FLEXIBLE SHIELDED POSITION SENSOR

(71) Applicant: BIOSENSE WEBSTER (ISRAEL) LTD., Yokneam (IL)

(72) Inventors: Vadim Gliner, Haifa (IL); Ilya Sitnitsky, Nahariya (IL)

(73) Assignee: Biosense Webster (Israel) Ltd., Yokneam (IL)

(*) Notice: Subject to any disclaimer, the term of this patent is extended or adjusted under 35 U.S.C. 154(b) by 469 days.

(21) Appl. No.: 16/571,320

(22) Filed: Sep. 16, 2019

(65) Prior Publication Data

US 2021/0076975 A1 Mar. 18, 2021

(51) Int. Cl.
| | | |
|---|---|---|
| *A61B 5/06* | | (2006.01) |
| *H05K 1/02* | | (2006.01) |
| *A61B 17/32* | | (2006.01) |
| *H01F 41/04* | | (2006.01) |
| *H05K 1/11* | | (2006.01) |
| *H01F 17/00* | | (2006.01) |

(52) U.S. Cl.
CPC .............. *A61B 5/062* (2013.01); *A61B 5/065* (2013.01); *A61B 17/320016* (2013.01); *H01F 17/0013* (2013.01); *H01F 41/041* (2013.01); *H05K 1/0218* (2013.01); *H05K 1/118* (2013.01)

(58) Field of Classification Search
CPC ........ A61B 5/062; A61B 5/065; H05K 1/118; H05K 1/0218
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 2003/0120150 A1 | 6/2003 | Govari |
| 2004/0068178 A1 | 4/2004 | Govari |
| 2013/0131496 A1 | 5/2013 | Jenkins et al. |
| 2013/0235550 A1 | 9/2013 | Stevenson et al. |
| 2014/0099595 A1 | 4/2014 | Taub |
| 2016/0007842 A1 | 1/2016 | Govari et al. |

(Continued)

FOREIGN PATENT DOCUMENTS

| | | |
|---|---|---|
| WO | WO 1996/005768 | 2/1996 |
| WO | WO 2014/143219 | 9/2014 |

OTHER PUBLICATIONS

European Search Report dated Dec. 1, 2020 from corresponding European Patent Application No. 20196283.4.

(Continued)

*Primary Examiner* — Jeremy C Norris
(74) *Attorney, Agent, or Firm* — Todd J. Burns

(57) ABSTRACT

In one embodiment, a medical device includes an instrument including a distal end configured for inserting into a body part, and a position sensor comprising a flexible printed circuit, which comprises alternating conductive and dielectric layers and is wrapped around the distal end of the instrument, the conductive layers including at least one inner layer, which is patterned with traces forming a coil, and multiple outer layers overlying the at least one inner layer and configured for connection to an electrical ground so as to shield the coil from electromagnetic interference.

16 Claims, 8 Drawing Sheets

(56) References Cited

U.S. PATENT DOCUMENTS

2016/0354160 A1   12/2016   Crowley et al.
2019/0175056 A1    6/2019   Berkowitz et al.

OTHER PUBLICATIONS

Yang, S. M. et al., "Electromagnetic shielding effectiveness of multilayer metallic thin film on plastic substrates", Journal of Applied Polymer Science, vol. 110, No. 3, Nov. 5, 2008, pp. 1403-1410.

Schlicke, H. M., "Simulated-skin-effect filters theory of simulated-skin-effect filters a thin film approach to EMI", IEEE Transactions on Electromagnetic Compatibility, Jan. 1, 1964, pp. 47-54.

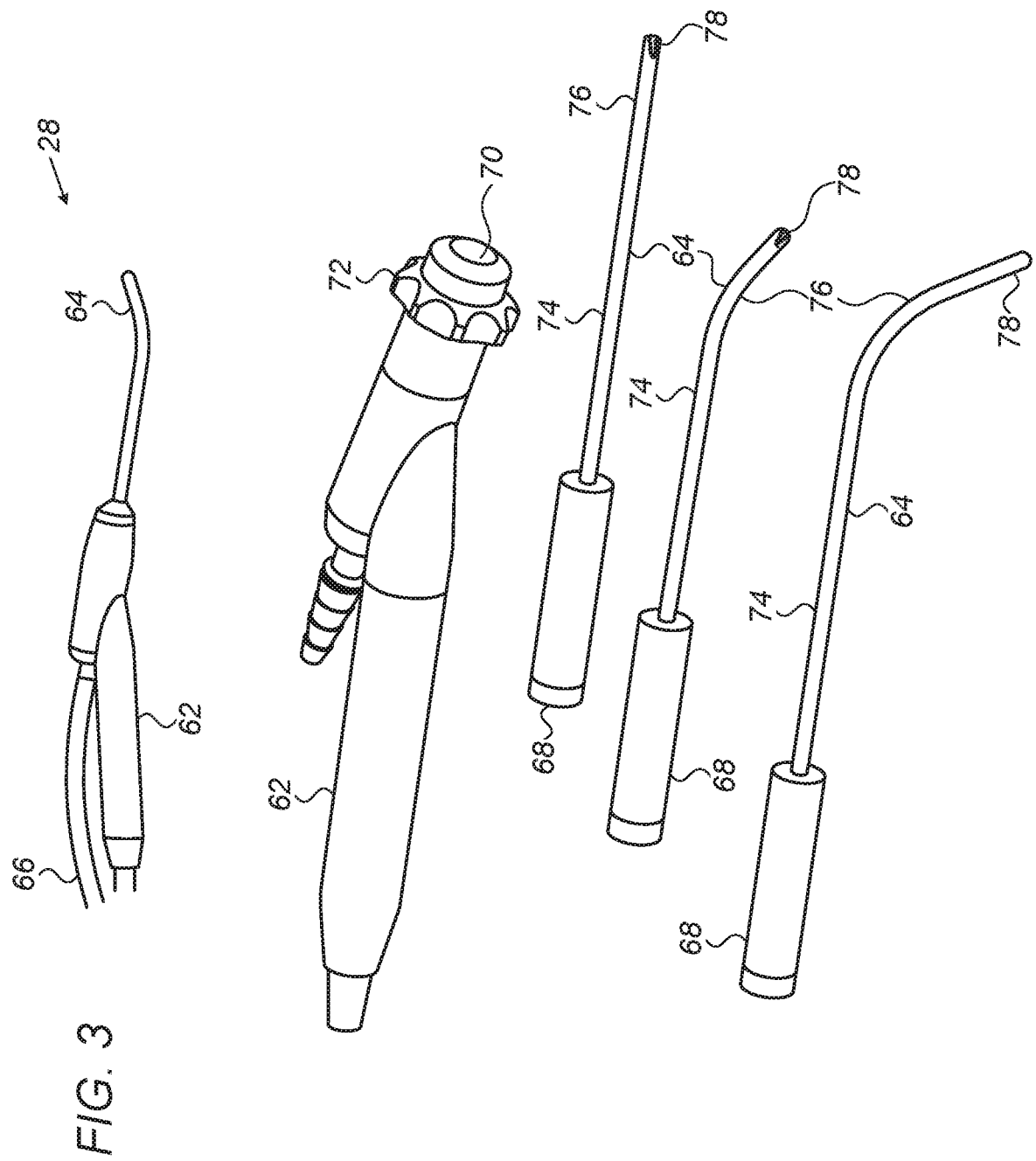

FLEXIBLE SHIELDED POSITION SENSOR

FIELD OF THE INVENTION

The present invention relates to medical devices, and in particular, but not exclusively to, position sensors for medical devices.

BACKGROUND

A wide range of medical procedures involve placing probes, such as guidewires and catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2003/0120150 and 2004/0068178, whose disclosures are all incorporated herein by reference.

US Patent Publication 2013/0131496 of Jenkins, et al., describes an MRI-compatible catheter that reduces localized heating due to MR scanner-induced currents includes an elongated flexible shaft having a distal end portion and an opposite proximal end portion. A handle is attached to the proximal end portion and includes an electrical connector interface configured to be in electrical communication with an MRI scanner. One or more RF tracking coils are positioned adjacent the distal end portion of the shaft. Each RF tracking coil includes a conductive lead, such as a coaxial cable, that extends between the RF tracking coil and the electrical connector interface and electrically connects the RF tracking coil to an MRI scanner. In some embodiments, the conductive lead has a length sufficient to define an odd harmonic/multiple of a quarter wavelength of the operational frequency of the MRI Scanner, and/or includes a series of pre-formed back and forth segments along its length.

US Patent Publication 2013/0235550 of Stevenson, et al., describes a shielded three-terminal flat-through EMI/energy dissipating filter includes an active electrode plate through which a circuit current passes between a first terminal and a second terminal, a first shield plate on a first side of the active electrode plate, and a second shield plate on a second side of the active electrode plate opposite the first shield plate. The first and second shield plates are conductively coupled to a grounded third terminal. In some embodiments, the active electrode plate and the shield plates are at least partially disposed with a hybrid flat-through substrate that may include a flex cable section, a rigid cable section, or both.

SUMMARY

There is provided in accordance with an embodiment of the present disclosure, a medical device, including an instrument including a distal end configured for inserting into a body part, and a position sensor including a flexible printed circuit, which includes alternating conductive and dielectric layers and is wrapped around the distal end of the instrument, the conductive layers including at least one inner layer, which is patterned with traces forming a coil, and multiple outer layers overlying the at least one inner layer and configured for connection to an electrical ground so as to shield the coil from electromagnetic interference.

Further in accordance with an embodiment of the present disclosure a combined thickness of the outer layers is in a range of 100 to 300 microns.

Still further in accordance with an embodiment of the present disclosure the instrument includes a proximal end, the position sensor including two electrical connections electrically connecting the coil with the proximal end, the multiple outer layers including elongated sections that overlay the electrical connections so as to shield the electrical connections from the electromagnetic interference.

Additionally, in accordance with an embodiment of the present disclosure the coil includes a major surface of which at least 90% is shielded by the multiple outer layers.

Moreover, in accordance with an embodiment of the present disclosure each of the multiple outer layers includes a major surface of which at least 90% is covered by a metal foil.

Further in accordance with an embodiment of the present disclosure the thickness of each of the multiple outer layers is in the range of 40 to 100 microns.

Still further in accordance with an embodiment of the present disclosure the coil is formed from a plurality of layers connected with vias.

Additionally, in accordance with an embodiment of the present disclosure the distal end of the instrument is formed as an elongated metal tool.

There is also provided in accordance with another embodiment of the present disclosure, a method of manufacturing a medical device, including forming a position sensor from a flexible printed circuit, which includes alternating conductive and dielectric layers, the conductive layers including at least one inner layer, which is patterned with traces forming a coil, and multiple outer layers overlying the at least one inner layer and configured for connection to an electrical ground so as to shield the coil from electromagnetic interference, wrapping the position sensor around a distal end of an instrument configured for inserting into a body part, and adhering the position sensor to the distal end.

Moreover, in accordance with an embodiment of the present disclosure a combined thickness of the outer layers is in a range of 100 to 300 microns.

Further in accordance with an embodiment of the present disclosure, the method includes forming the flexible printed circuit so that the multiple outer layers include elongated portions that overlay electrical connections from the coil to a proximal end of the instrument so as to shield the electrical connections from the electromagnetic interference.

Still further in accordance with an embodiment of the present disclosure the coil includes a major surface of which at least 90% is shielded by the multiple outer layers.

Additionally, in accordance with an embodiment of the present disclosure each of the multiple outer layers includes a major surface of which at least 90% is covered by a metal foil.

Moreover, in accordance with an embodiment of the present disclosure the thickness of each of the multiple outer layers is in the range of 40 to 100 microns.

Further in accordance with an embodiment of the present disclosure the coil is formed from a plurality of layers connected with vias.

Still further in accordance with an embodiment of the present disclosure the distal end of the instrument is formed as an elongated metal tool.

BRIEF DESCRIPTION OF THE DRAWINGS

The present invention will be understood from the following detailed description, taken in conjunction with the drawings in which:

FIG. 3 is a schematic view of a medical instrument for use in the system of FIG. 1;

FIG. 4 shows a handle and interchangeable heads of the medical instrument of FIG. 3;

DESCRIPTION OF EXAMPLE EMBODIMENTS

Overview

Figure 1:
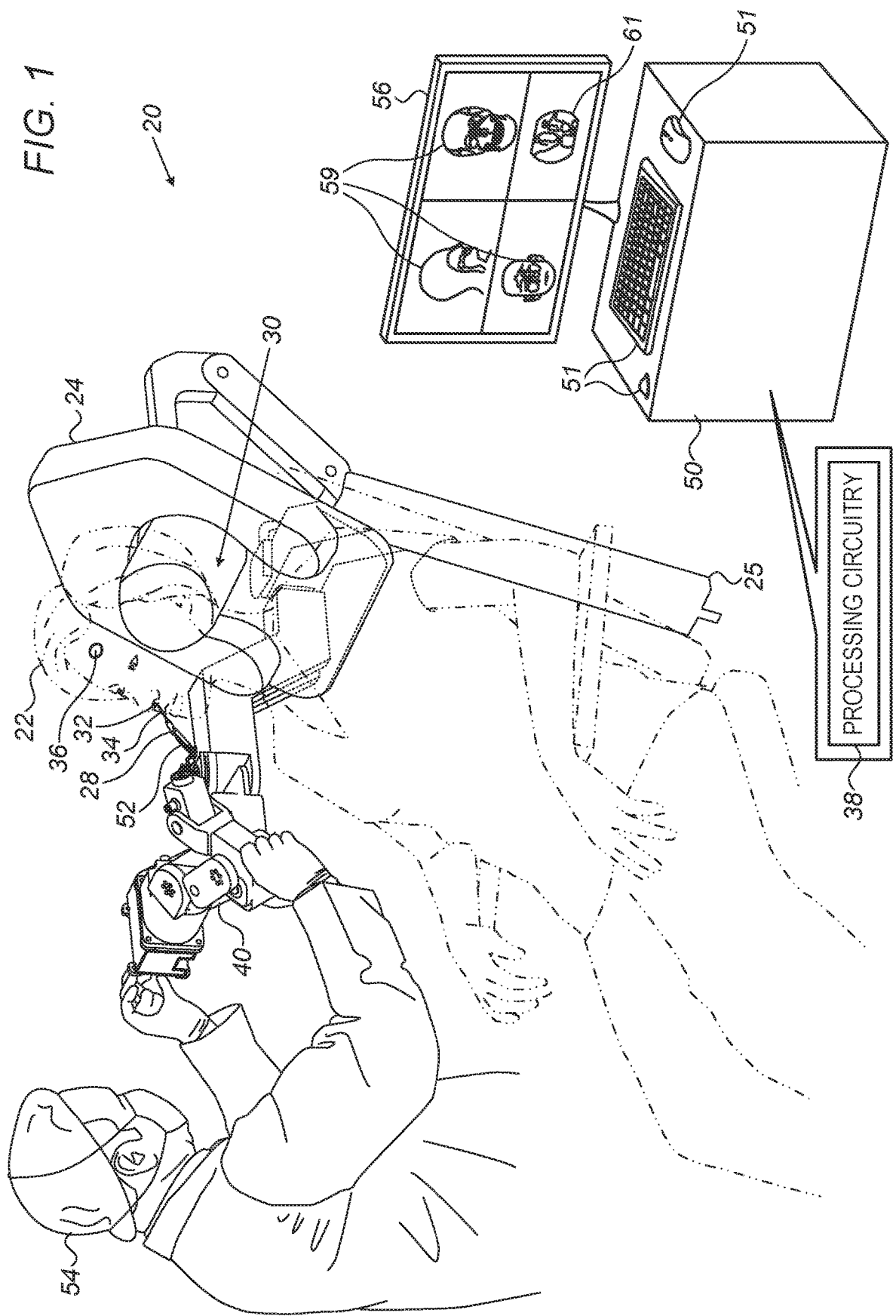
FIG. 1 is a schematic illustration of a medical procedure system, according to an embodiment of the present invention.

In a medical instrument, for example, a cardiac catheter, which is navigated using a magnetic coil sensor, the coil may be covered with one or more metal electrodes, e.g., ablation or mapping electrodes, which apart from performing their primary function (e.g., ablation or mapping), also act as a radio frequency (RF) shield for the magnetic sensor in the instrument. However, for other medical instruments, such as, an ENT tool or a guidewire, which do not include a metal electrode covering the magnetic sensor, the magnetic sensor may be exposed to unwanted electromagnetic interference (e.g., from RF sources). For example, if the sensor is operating at 20 kHz and an analog-to-digital convertor in the vicinity is switched at 120 kHz, some of the switching frequency signal may be acquired by the sensor. This sort of interference drastically reduces the efficiency of the sensor. Additionally, as the signal amplitude of the interference may be much higher than the signal amplitude of the magnetic signals used in the tracking of the magnetic sensor, using an electronic low pass filter may be insufficient to remove the interference from the signals detected by the sensor. Although, covering the magnetic sensor with a metal cap may provide some shielding, securing a metal cap over the magnetic sensor may be impractical in many implementations.

Embodiments of the present invention solve the above problems by providing a medical device comprising an instrument and a position sensor, which includes a flexible printed circuit having alternating conductive and dielectric layers, and is wrapped around, and adhered to, the distal end of the instrument. The conductive layers include at least one inner layer, which is patterned with traces forming a coil, and multiple outer layers overlying the inner layer(s), which are connected to an electrical ground during operation of the medical device so as to shield the coil from electromagnetic interference. Each of the outer conductive layers is disposed on one of the dielectric layers and may be formed from a "raw" printed circuit board (PCB) layer, including a dielectric base, such as, as polymer, covered with a conductive layer, such as, copper foil.

As the outer layers are connected and grounded, these layers effectively act as a single thick conductive layer providing electromagnetic shielding according to the thickness of the combined outer layers. In some embodiments, the combined thickness of the outer layers is in the range of 100 to 300 microns. In other embodiments, the combined thickness of the outer layers may be less than 100 micros or more than 300 microns. The penetration of an electromagnetic signal through the outer layers is a function of the frequency of the signal (the higher the frequency, the shorter the distance the signal can penetrate for a given thickness of conductor). Therefore, the thickness and/or number of outer layers can be selected so that the operating frequency of the sensor (e.g. 20 kHz) sufficiently penetrates the outer layers, while higher "interfering" frequencies (e.g., 120 kHz) are sufficiently attenuated. For example, the "skin depth" of copper, at which the current density falls to about 1/e of its initial value is about 188 microns at 120 kHz, and 460 microns at 20 kHz. Therefore, using four copper layers of 50 microns thickness each will significantly reduce (to around 1/e) the 120 kHz signals picked up by the coil, while allowing a significant amount of the 20 kHz signals to be detected by the coil. The multiple connected outer layers effectively act as a physical low-pass filter, allowing the low frequency signals to pass and blocking (or reducing) higher frequency signals. The multiple layers thus act as a frequency-selective RF shield for the position sensor. The thickness and/or number of outer conductive layers may be selected while still maintaining sufficient flexibility in the flexible printed circuit so as to wrap the flexible printed circuit around the distal end.

In some embodiments, the distal end of the instrument is formed as an elongated metal tool. In other embodiments the distal end may be formed from any suitable material.

The coil may be formed as a single layer coil or a multi-layer coil, which has the different PCB layers being connected with vias. In some embodiments, the coil includes a major surface of which at least 90% is shielded by the multiple outer layers. In some embodiments, each outer layer comprises a major surface of which at least 90% is covered by a metal foil, e.g., copper foil. The thickness of each of the outer conductive layers may be in the range of 40 to 100 microns, by way of example only. The term "major surface" as used in the specification and claims is defined herein as a surface which is parallel to the planes of the layers of flexible printed circuit prior to the flexible printed circuit being wrapped around the distal end of the instrument.

In some embodiments, the position sensor includes two electrical connections electrically connecting the coil with the proximal end of the instrument while the outer layers include elongated sections that overlay the electrical connections so as to shield the electrical connections from the electromagnetic interference.

In some embodiments, the medical device may also include one or more magnetic-field radiators to radiate at least one alternating magnetic field of at least one frequency for detection by the coil. The number and/or thickness of the outer conductive layers of the position sensor may be selected so as to configure the outer layers as a low-pass filter, which filters at least some of the electromagnetic interference while still allowing transmission of signals of the frequency (frequencies) radiated by the magnetic-field radiator(s). Additionally, or alternatively, the number and/or thickness of the outer conductive layers is selected to minimize the electromagnetic interference while still maintaining sufficient flexibility in the flexible printed circuit so as to wrap the flexible printed circuit around the distal end.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
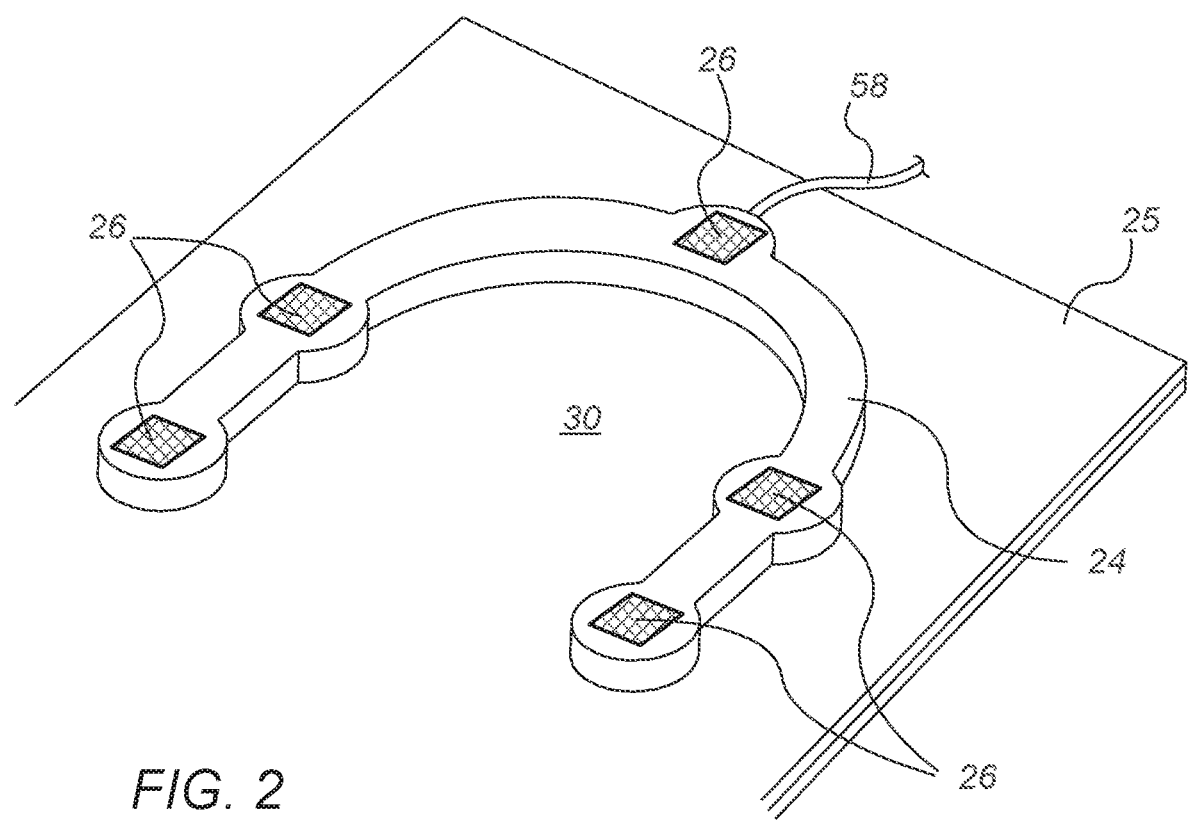
FIG. 2 is a schematic illustration of a magnetic field radiation assembly used in the medical procedure system, according to an embodiment of the present invention.

Turning now to the drawings, reference is now made to FIG. 1, which is a schematic illustration of a medical procedure system 20, and to FIG. 2, which is a schematic illustration of a magnetic field radiation assembly location pad 24 used in the system 20, according to an embodiment of the present invention. The medical procedure system 20 is typically used during an invasive and/or investigative procedure on a nasal sinus or another body part (such as the brain) of a patient 22.

For the procedure, the magnetic field radiation assembly 24 may be positioned behind and/or around the head of the patient 22, for example by fixing the assembly 24 to a chair 25 (or bed) upon which the patient is sitting (or lying). The magnetic field radiation assembly 24 in the pictured example comprises five magnetic field radiators 26, which are fixed in a horseshoe shaped frame, the frame being positioned beneath or around the patient 22 so that the magnetic field radiators 26 surround the head of the patient 22. Alternatively, smaller or larger numbers of radiators 26 may be used, in various different configurations. The magnetic field radiators 26 are configured to radiate alternating magnetic fields at respective frequencies into a region 30 where the body part is located, in proximity to the magnetic field radiation assembly 24 and which includes the head of patient 22.

The alternating magnetic fields induce signals in a position sensor 32 and a position sensor 36. The position sensor 32 is shown disposed on a medical instrument 28 in order to track a position of the medical instrument 28. The position sensor 36 is shown disposed on the patient 22 (e.g., on the forehead of the patient 22 or any other suitable body part) in order to track a position of the patient 22 (e.g., to track a position of the head of the patient 22) to compensate for movement of the patient with respect to the magnetic field radiation assembly 24. By way of example only, the medical instrument 28 may include any one or more of the following, a probe for inserting into the body-part, an endoscope, and/or a surgical tool such as an ENT tool, suction tool, microdebrider, or a shaver.

The position of the distal end of the medical instrument 28 and the position of the patient 22, may be tracked using a tracking subsystem, which tracks position and orientation coordinates of the position sensor 32 fitted at the distal end and the position sensor 36, respectively. The position sensors 32, 36 are configured to output signals that are indicative of locations of the sensors 32, 36, respectively. The signals are processed by the tracking subsystem running on processing circuitry 38 to track the locations of the distal end of the medical instrument 28 and the position of the patient 22 over time. In embodiments, where the tracking subsystem is a magnetic tracking subsystem, the position sensor 32 and/or the position sensor 36 includes at least one coil, described in more detail with reference to FIG. 5-9. Using tracking subsystem, a physician 54 advances the distal end of the medical instrument 28 in a body-part, described in more detail below.

In some embodiments, the medical instrument 28 is attached to, and held by, a robotic arm 40, which is configured to manipulate the medical instrument 28. The robotic arm 40 includes a plurality of robotic joints configured to control movement of the robotic arm 40 and manipulate the medical instrument 28. In other embodiments, the medical instrument 28 is held and manipulated by the physician 54.

As is described in more detail below, position sensor 32 is affixed to the medical instrument 28, and determination of the location and orientation of the position sensor 32 enables tracking the location and orientation of a distal end 34 (or other location) of the medical instrument 28, which may be reversibly inserted into a body-part of the patient 22 (the living subject).

Similarly, determination of the location and orientation of the position sensor 36 enables the location and orientation of a part (e.g., the head) of the patient 22 to be tracked. The position sensor 36 is shown in FIG. 1 as being disposed on the forehead of the patient 22. The position sensor 36 may be disposed on any other suitable body part of the patient 22 in order to track the position/movement of the patient 22.

A system using magnetic field radiators, such as the magnetic field radiators 26, for tracking an entity inserted into a patient is described in US Patent Publication 2016/0007842, of Govari et al., which is incorporated herein by reference. In addition, the Carto® system produced by Biosense Webster of 33 Technology Drive, Irvine, Calif. 92618 USA, uses a tracking system similar to that described herein for finding the location and orientation of a coil in a region irradiated by magnetic fields.

The robotic arm 40 generally has its own robotic coordinate system. The robotic coordinate system is registered with a magnetic coordinate system of the magnetic field radiators 26 or vice-versa. Registration of the robotic coordinate system with the magnetic coordinate system may be performed, for example, by moving the robotic arm 40, or the medical instrument 28 attached to the robotic arm 40, to one or more locations known to the magnetic field radiators 26, for example, to a location on the magnetic field radiation assembly 24 or to the position sensor 36 or to one or more other known locations on the patient 22. Once registration of the robotic coordinate system with the magnetic coordinate system has been performed, locations in the magnetic coordinate system can be translated to the robotic coordinate system in order to manipulate the robotic arm 40 correctly.

Elements of system 20, including radiators 26, may be controlled by the processing circuitry 38, which comprises a processing unit communicating with one or more memories. Typically, the elements may be connected by cables to the processing circuitry 38, for example, radiators 26 may be connected by a cable 58 to the processing circuitry 38. Alternatively, or additionally, the elements may be coupled wirelessly to the processing circuitry 38. The processing circuitry 38 may be mounted in a console 50, which comprises operating controls 51 that typically include a keypad and/or a pointing device such as a mouse or trackball. The console 50 also connects to other elements of the medical procedure system 20, such as a proximal end 52 of the medical instrument 28. A physician 54 uses the operating controls 51 to interact with the processing circuitry 38 while performing the procedure, and the processing circuitry 38 may present results produced by system 20 on a display 56.

In some embodiments, prior to performing the medical procedure, CT images of the patient 22 are acquired. The CT images are stored in a memory (not shown) for subsequent retrieval by the processing circuitry 38. In FIG. 1, the display 56 is shown displaying various views 59 of a previous CT scan (or other suitable scan) which may be used as an aid for the physician 54 to guide the medical instrument 28 in the body-part. The display screen 56 also shows an image 61 captured by a camera (not shown) of the medical instrument 28. The CT images may be registered with the magnetic coordinate system so that a representation of the medical instrument 28 may be displayed with the CT images on the display 56.

In practice, some or all of these functions of the processing circuitry 38 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Reference is now made to FIG. 3, which is a schematic view of the medical instrument 28 for use in the system 20 of FIG. 1. The medical instrument 28 includes a handle 62 in which a plurality of different rigid interchangeable heads 64 are individually reversibly insertable. FIG. 3 shows one of the interchangeable heads 64 inserted into the handle 62. Other ones of the interchangeable heads 64 are shown in FIG. 4, which is described hereinbelow. The medical instrument 28 shown in FIG. 3 also includes an irrigation or drainage tube 66. Each interchangeable head 64 representing the distal end of the medical instrument 28 may be formed as an elongated tool, formed from any suitable material, for example, but not limited to, a metal such as stainless steel, or a plastic such as a biocompatible plastic. In some embodiments, the interchangeable heads 64 may be flexible or deflectable.

The medical instrument 28 shown in FIG. 3 is shown prior to any position sensors being added to the medical instrument 28. In fact, in some embodiments, the medical instrument 28 may be implemented with an off-the-shelf medical instrument which is sold without position sensors and to which position sensors are added at appropriate positions, as will be described below with reference to FIG. 5. For example, the S120 hand-piece and interchangeable reusable blades of Bien Air®, which is available without position sensors, may be adapted to provide the medical instrument 28 described hereinbelow. In other embodiments, the medical instrument 28 may be implemented as a purpose-built medical instrument with integral position sensors.

Reference is now made to FIG. 4, which shows the handle 62 and multiple different interchangeable heads 64 of the medical instrument 28 of FIG. 3. The handle 62 and the interchangeable heads 64 shown in FIG. 4 are also shown without the position sensors. The interchangeable heads 64 are different from each other with respect to a head shape and/or a head size.

Each interchangeable head 64 includes a plastic proximal end 68 which is inserted into a socket 70 of the handle 62. The socket 70 of the handle 62 includes multiple rotational positions in which to insert the different rigid interchangeable heads 64. For example, with the S120 hand-piece, the reusable blades may be inserted in eight different rotational positions. In some embodiments, the interchangeable heads 64 may be inserted into the socket 70 in a single rotational position.

The handle 62 includes multiple rotational positions to which to rotate the different rigid interchangeable heads 64. Therefore, once one of the interchangeable heads 64 has been inserted into the socket 70, the inserted interchangeable head 64 may be rotated to multiple rotational positions using a rotational adjustment cog wheel 72. In other embodiments, the inserted interchangeable head 64 cannot be rotated to another position.

In the example of FIG. 4, each of the interchangeable heads 64 is implemented with an elongated shaft 74 having a distal end 76, which includes at least one cutting element 78 disposed at the distal end 76 of the elongated shaft 74. The cutting element(s) 78 may include a shaving bur (e.g., a rough surface cylindrical shape or ball shape element) or a shaving blade rotating inside the elongated shaft 74 or any other suitable cutting element.

Figure 5:
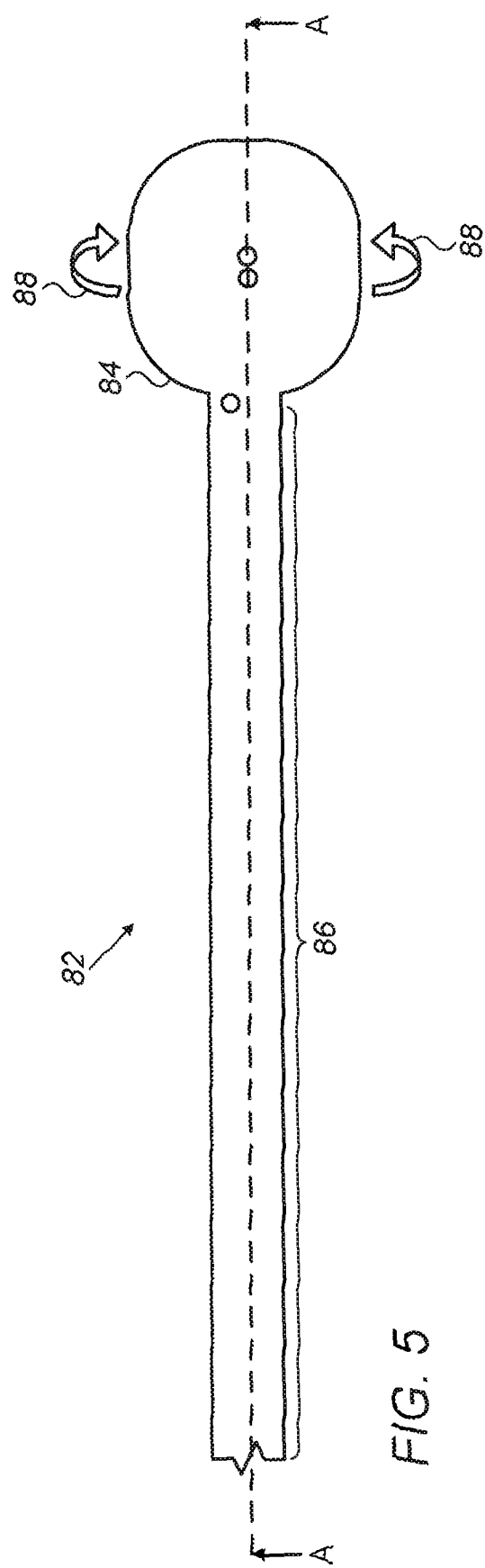
FIG. 5 is a plan view of a sensor for use with the medical instrument of FIG. 3.
Figure 6:
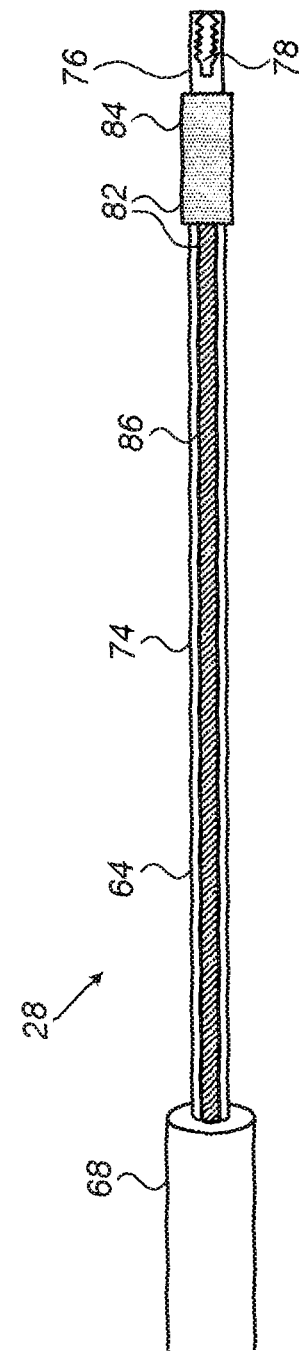
FIG. 6 is a schematic view of the sensor of FIG. 5 disposed on one of the interchangeable heads of the medical instrument of FIG. 3.

Reference is now made to FIG. 5, which is a plan view of a sensor 82 for use with the medical instrument 28 of FIG. 3. The sensor 82 includes a distal end 84 which includes at least one coil (not shown in FIG. 5) disposed therein, and shielding layers to shield the coil from electromagnetic interference, described in more detail with reference to FIGS. 7-9. The sensor 82 may be a single axis, a dual axis, or a triple axis sensor, using one, two, or three coils, respectively. The sensor 82 also includes an elongated section 86 including shielded electrical connections electrically connecting the coil(s) with a proximal end of the medical instrument 28, also described in more detail with reference to FIGS. 7-9. The sensor 82 is adhered to one of the interchangeable heads 64 (FIG. 4) so that the distal end 84 of the sensor 82 is wrapped around the distal end 76 of that interchangeable head 64 as indicated by arrows 88, and the elongated section 86 extends from the distal end 76 of that interchangeable head 64 towards the proximal end 68 of that interchangeable head 64 as shown in FIG. 6. The term "wrapped" as used in the specification and claims, in all grammatical forms, is defined as partially or fully encircling the distal end 76 of the medical instrument 28 with the distal end 84 of the sensor 82. The elongated section 86 is shown as being centrally disposed with respect to the distal end 84 of the sensor 82. In some embodiments, the elongated section 86 may be disposed in an off-center spatial relation with respect to the distal end 84 of the sensor 82.

Reference is now made to FIG. 6, which is a schematic view of the sensor 82 of FIG. 5 disposed on one of the interchangeable heads 64 of the medical instrument 28 of FIG. 3. In some embodiments, the sensor 82 may be disposed on the distal end of any suitable medical instrument, even an instrument without an interchangeable head, and/or on a distal end formed from any suitable material, such as metal or plastic. The sensor 82 may be disposed on any suitable medical instrument, for example, but not limited to, including any one or more of the following, a probe for inserting into a body-part, an endoscope, and/or a surgical tool such as an ENT tool, suction tool, microdebrider, or a shaver. The sensor 82 may be disposed on the distal end of a tool having a rigid, or flexible, or deflectable distal end. The sensor 82 is configured to detect at least part of the transmitted alternating magnetic fields of the magnetic field radiators 26 (FIG. 2). Additional positions sensors (single, dual or triple axis sensors) may be disposed on the interchangeable head 64 and/or the handle 62 (FIGS. 3 and 4).

The position sensor 82 is electrically insulated from the elongated shaft 74 and the cutting element(s) 78, for example, using an insulating layer of the sensor 82 as described in more detail with reference to FIGS. 7-9. In some embodiments where the sensor 82 includes the distal end 84 without the elongated section 86, wires extending from the sensor 82 may be secured, for example using self-adhesive tape (not shown), to the elongated shaft 74.

At least some of the elongated shaft 74 may be disposed in a plastic biocompatible sleeve (not shown) prior to inserting the elongated shaft 74 in a body part. In some embodiments, the sleeve may cover the elongated shaft 74 from the plastic proximal end 68 up to and including the distal end 84 of the head position sensor 82.

Figure 7:
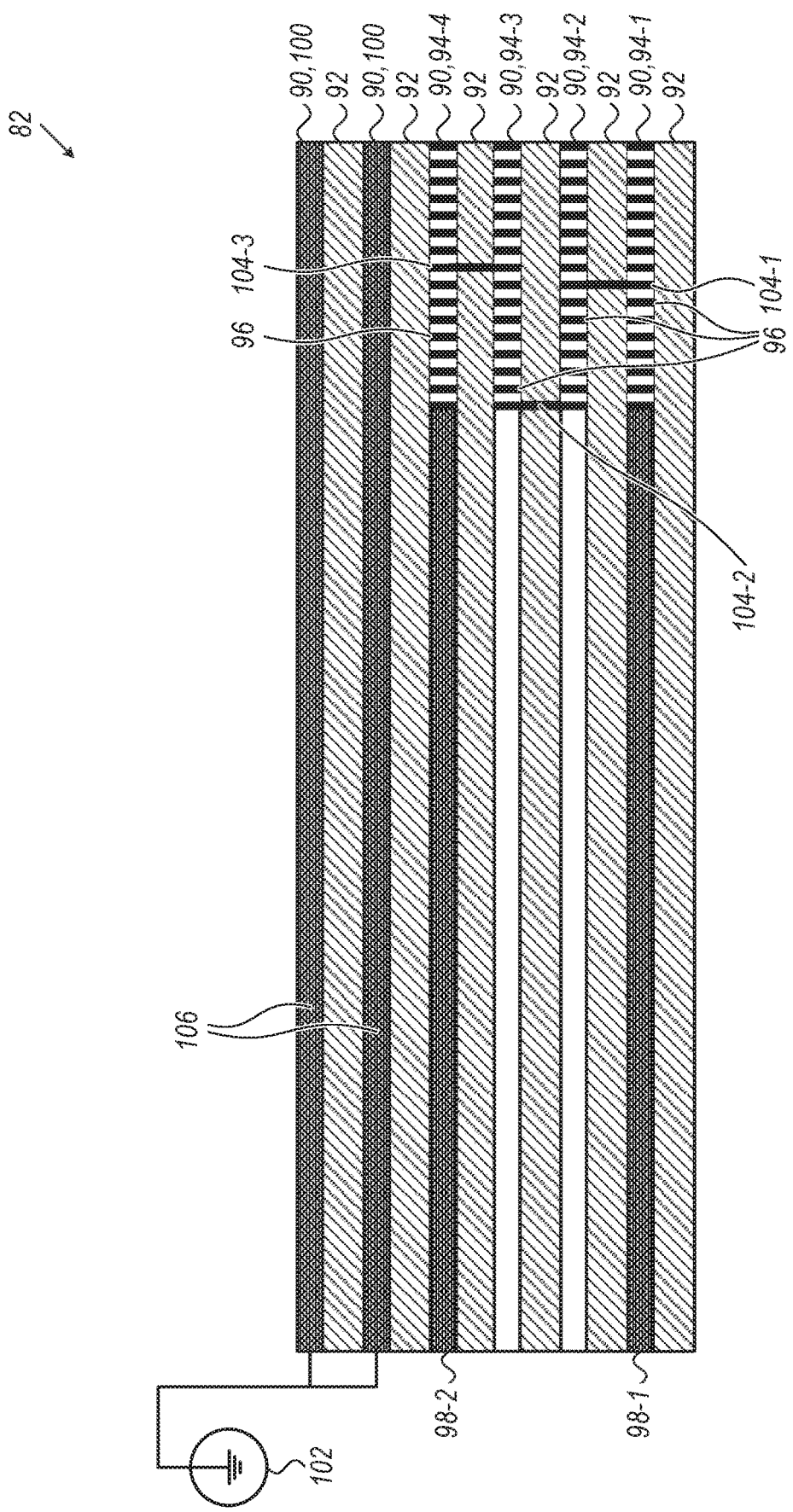
FIG. 7 is a cross-sectional view of the sensor of FIG. 5 through line A:A.

Reference is now made to FIG. 7, which is a cross-sectional view of the sensor 82 of FIG. 5 through line A:A. The sensor 82 includes a flexible printed circuit, which comprises alternating conductive layers 90 and dielectric layers 92. The sensor 82 shown in FIG. 7 includes six conductive layers 90 and six dielectric layers 92. The conductive layers 90 include at least one inner layer 94, which is patterned with traces forming a coil 96. The conductive layers 90 includes multiple outer layers 100 overlying the inner layer(s) 94 and configured for connection to an electrical ground 102 so as to shield the coil 96 from electromagnetic interference.

In the example of FIG. 7 the coil 96 is formed on four inner layers 94-1 to 94-4 connected by vias 104. In some embodiments, the coil 96 may be formed from one, two, three, or any suitable number of layers 94. The bottom inner layer 94-1 includes a part of the coil 96 and an electrical connection 98-1 to connect the part of the coil 96 disposed on the inner layer 94-1 to an electrical connection near the proximal end 68 (FIG. 6) of head 64 (FIG. 6). The inner layer 94-2 above the inner layer 94-1 includes another part of the coil 96, which is connected to the part of the coil 96 of the inner layer 94-1 using a via 104-1. The inner layer 94-3 above the inner layer 94-2 includes another part of the coil 96, which is connected to the part of the coil 96 of the inner layer 94-2 using a via 104-2. The top inner layer 94-4 above the inner layer 94-3 includes another part of the coil 96, which is connected to the part of the coil 96 of the inner layer 94-3 using a via 104-3. The inner layer 94-4 also includes an electrical connection 98-2 to connect the coil 96 disposed on the inner layer 94-4 to an electrical connection (not shown) near the proximal end 68 of head 64.

Each of the conductive inner layers 94 may be formed by selectively etching the conductive layer 90 of a conductive-dielectric layer pair 90, 92. The etched conductive-dielectric layer pairs 90, 92 are suitably connected and the vias 104 are suitably installed. Each of the conductive outer layers 100 may be formed by using an un-etched or "raw" conductive-dielectric layer pair 90, 92. The conductive layers 90 may be formed from a flexible metal foil, for example, but not limited to, a copper foil. The dielectric layers 92 may be formed from a flexible insulator, for example, but not limited to, a polymer. Each conductive outer layer 100 may have any suitable thickness, for example, but not limited to, in the range of 40 to 100 microns.

As the multiple conductive outer layers 100 are connected and grounded, these layers 100 effectively act as one thick conductive layer providing electromagnetic shielding. In some embodiments, the combined thickness of the conductive outer layers is in the range of 100 to 300 microns. In other embodiments, the combined thickness of the conductive outer layers may be less than 100 micros or more than 300 microns. The penetration of an electromagnetic signal through the outer layers 100 is a function of the frequency of the signal (the higher the frequency, the shorter the distance the signal can penetrate for a given thickness of conductor). The thickness and/or number of outer layers 100 may be selected so as to configure the outer layers 100 as a low-pass filter, which filters at least some of the electromagnetic interference while still allowing transmission of signals of the frequency (or frequencies) radiated by the magnetic radiators 26 (FIG. 2). In such a manner, the operating frequency of the sensor (e.g. 20 kHz) sufficiently penetrates the outer layers 100, while higher "interfering" frequencies (e.g., 120 kHz) are sufficiently attenuated. For example, the skin depth of copper, at which the current density falls to about 1/e is about 188 microns at 100 kHz, and 460 microns at 20 kHz. Therefore, using four copper layers of 50 microns thickness will significantly reduce (to around 1/e) the 120 kHz signals picked up by the coil 96, while allowing a significant amount of the 20 kHz signals to be detected by the coil 96. Additionally, or alternatively, the thickness and/or number of outer conductive layers 100 may be selected to minimize the electromagnetic interference while still maintaining sufficient flexibility in the flexible printed circuit so as to wrap the flexible printed circuit around the distal end 76 of the medical instrument 28 (FIG. 6).

The electrical connections 98 from the coil 96 are also shielded from electromagnetic interference. The outer layers 100 include elongated sections 106 corresponding with the elongated section 86 (FIG. 5) that overlay the electrical connections 98 so as to shield the electrical connections 98 from the electromagnetic interference.

Figure 8:
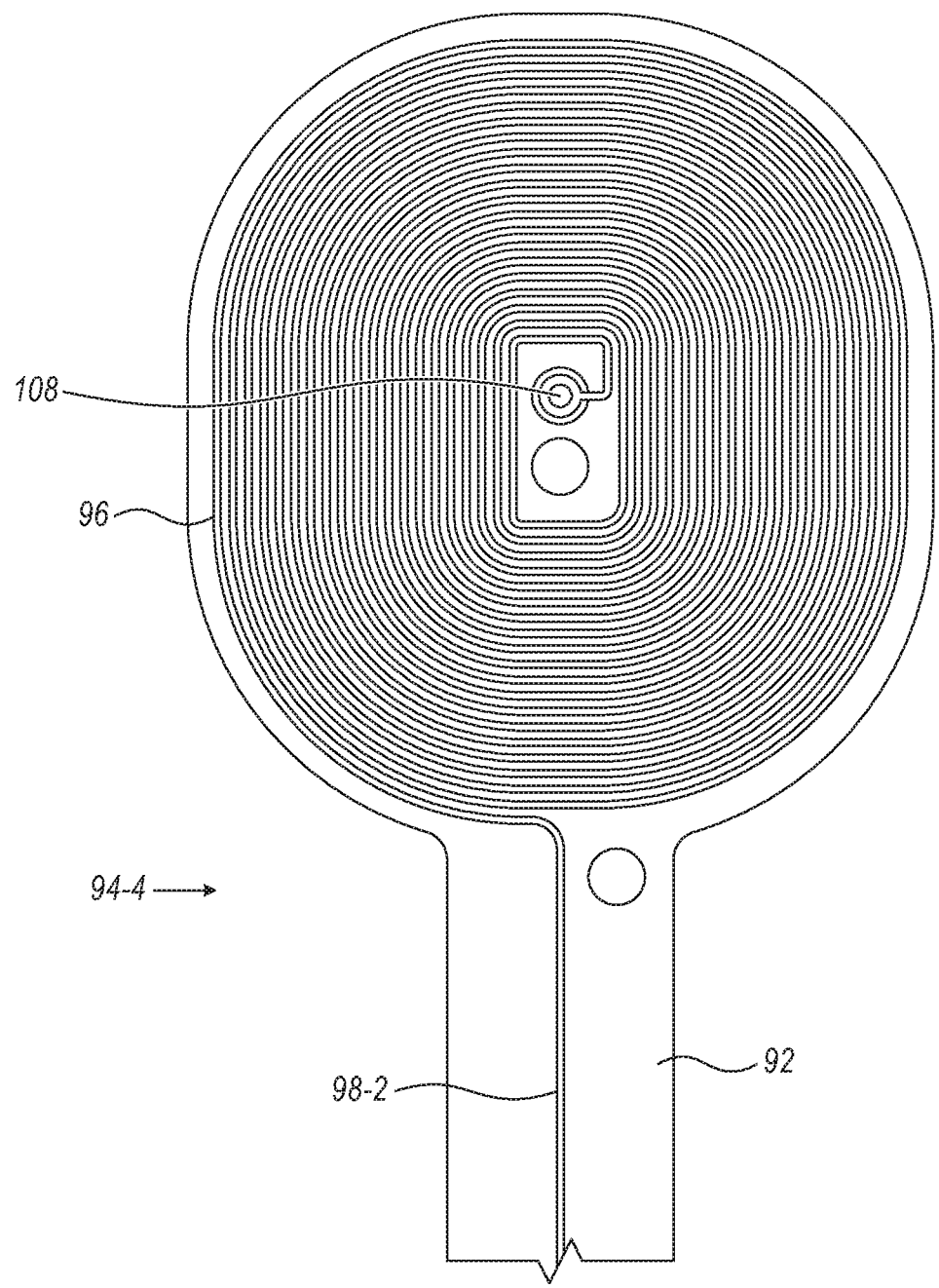
FIG. 8 is a plan view of one of the layers of the sensor of FIG. 5.

Reference is now made to FIG. 8, which is a plan view of the inner layer 94-4 of the sensor 82 of FIG. 5. FIG. 8 shows the traces of part of the coil 96, the electrical connection 98-2, and a connection 108 to the via 104-3, which are formed after etching the conductive layer 90 (FIG. 7) to reveal the dielectric layer 92 beneath the conductive layer 90 around the coil traces and connections 98-2, 108. The other inner layers 94 may be similarly formed.

Figure 9:
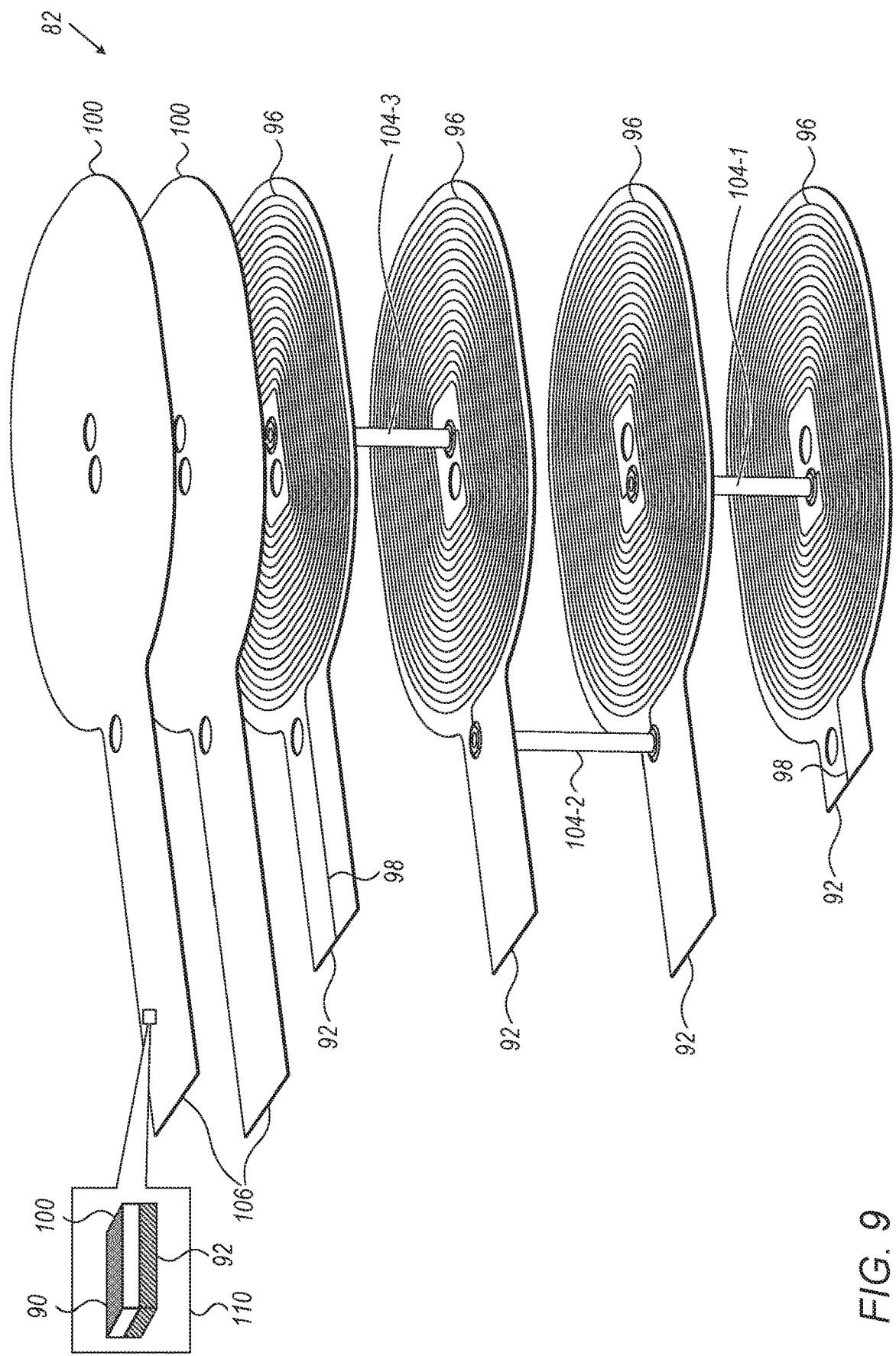
FIG. 9 is an exploded view of the sensor of FIG. 5.

Reference is now made to FIG. 9, which is an exploded view of the sensor 82 of FIG. 5. FIG. 9 shows the parts of the coil 96 formed on four dielectric layers 92 and connected with the vias 104. Only part of the electrical connections 98 and the elongated sections 106 are shown in FIG. 9 for the sake of simplicity. Each outer conductive outer layer 100 is formed from a conductive-dielectric layer pair 90, 92 (as shown in inset 110). The coil 96 is generally shielded from on top by the outer layers 100. In some embodiments, the coil 96 includes a major surface of which at least 90% (e.g., 100%) is shielded by the multiple outer layers 100. Each outer layer 100 is generally covered with a conductor such as a metal foil, e.g., a copper foil. In some embodiments, each outer layer 100 comprises a major surface of which at least 90% (e.g., 100%) is covered by a metal foil, e.g., copper foil.

Figure 10:
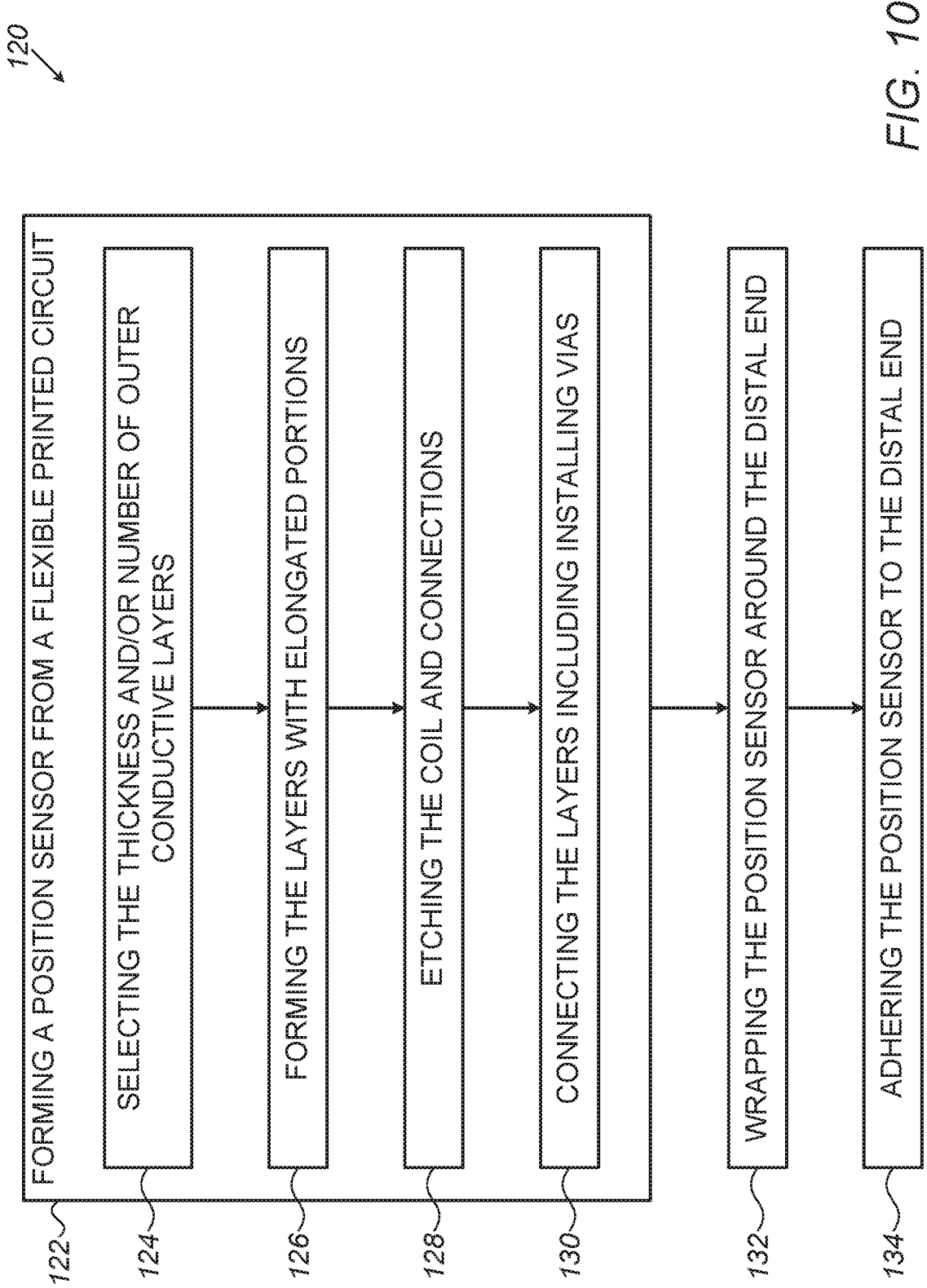
FIG. 10 is a flowchart including steps in a method of manufacturing a medical device according to an embodiment of the present invention.

Reference is now made to FIG. 10, is a flowchart 120 including steps in a method of manufacturing a medical device according to an embodiment of the present invention. Reference is also made to FIGS. 6 and 7. The method includes forming (block 122) the position sensor 82 from a flexible printed circuit, which comprises alternating conductive and dielectric layers 90, 92. The conductive layers 90 include: at least one inner layer 94, which is patterned with traces forming the coil 96; and multiple outer layers 100 overlying the at least one inner layer 94 and configured for connection to the electrical ground 102 so as to shield the coil 96 from electromagnetic interference. The step of block 122 includes a number of sub-steps described below with reference to blocks 124-130.

One of the sub-steps includes selecting (block 124) the thickness and/or number of outer layers 100 so as to configure the outer layers 100 as a low-pass filter, which filters at least some of the electromagnetic interference while still allowing transmission of signals of at least one frequency used by the position sensor 82, and/or minimize the electromagnetic interference while still maintaining sufficient flexibility in the flexible printed circuit so as to wrap the flexible printed circuit around the distal end 76. One of the sub-steps includes forming (block 126) the flexible printed circuit so that the multiple outer layers 100 include elongated portions 106 that overlay electrical connections 98 from the coil 96 to the proximal end 68 of the instrument 28 so as to shield the electrical connections 98 from the electromagnetic interference. One of the sub-steps includes etching (block 128) the coil 96 and the electrical connection 98 from the respective conductive-dielectric layer pairs 90, 92. One of the sub-steps also includes connecting (block 130) the layer pairs 90, 92 together and installing the vias 104.

The method also includes wrapping (block 132) the position sensor 82 around the distal end 76 of the medical instrument 28 and adhering (block 134) the position sensor to the distal end.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical device, comprising:
   an instrument including a distal end configured for inserting into a body part; and
   a position sensor comprising a flexible printed circuit, which comprises alternating conductive and dielectric layers and is wrapped around the distal end of the instrument, the conductive layers including:
   at least one inner layer, which is patterned with traces forming a coil; and
   multiple outer layers overlying the at least one inner layer and configured for connection to an electrical ground so as to shield the coil from electromagnetic interference.

2. The device according to claim 1, wherein a combined thickness of the outer layers is in a range of 100 to 300 microns.

3. The device according to claim 1, wherein the instrument includes a proximal end, the position sensor comprising two electrical connections electrically connecting the coil with the proximal end, the multiple outer layers including elongated sections that overlay the electrical connections so as to shield the electrical connections from the electromagnetic interference.

4. The device according to claim 1, wherein the coil includes a major surface of which at least 90% is shielded by the multiple outer layers.

5. The device according to claim 1, wherein each of the multiple outer layers comprises a major surface of which at least 90% is covered by a metal foil.

6. The device according to claim 1, wherein the thickness of each of the multiple outer layers is in the range of 40 to 100 microns.

7. The device according to claim 1, wherein the coil is formed from a plurality of layers connected with vias.

8. The device according to claim 1, wherein the distal end of the instrument is formed as an elongated metal tool.

9. A method of manufacturing a medical device, comprising:
   forming a position sensor from a flexible printed circuit, which comprises alternating conductive and dielectric layers, the conductive layers including:
   at least one inner layer, which is patterned with traces forming a coil; and
   multiple outer layers overlying the at least one inner layer and configured for connection to an electrical ground so as to shield the coil from electromagnetic interference;
   wrapping the position sensor around a distal end of an instrument configured for inserting into a body part; and
   adhering the position sensor to the distal end.

10. The method according to claim 9, wherein a combined thickness of the outer layers is in a range of 100 to 300 microns.

11. The method according to claim 9, further comprising forming the flexible printed circuit so that the multiple outer layers include elongated portions that overlay electrical connections from the coil to a proximal end of the instrument so as to shield the electrical connections from the electromagnetic interference.

12. The method according to claim 9, wherein the coil includes a major surface of which at least 90% is shielded by the multiple outer layers.

13. The method according to claim 9, wherein each of the multiple outer layers comprises a major surface of which at least 90% is covered by a metal foil.

14. The method according to claim 9, wherein the thickness of each of the multiple outer layers is in the range of 40 to 100 microns.

15. The method according to claim 9, wherein the coil is formed from a plurality of layers connected with vias.

16. The method according to claim 9, wherein the distal end of the instrument is formed as an elongated metal tool.

* * * * *